United States Patent [19]

Mets et al.

[11] Patent Number: 5,332,408
[45] Date of Patent: Jul. 26, 1994

[54] METHODS AND REAGENTS FOR BACKCROSS BREEDING OF PLANTS

[75] Inventors: Laurens J. Mets, Wilmette; Sharon A. Rogers, Grayslake; Mark J. Reichardt, LaGrange Park, all of Ill.

[73] Assignee: Lakeside Biotechnology, Inc., Chicago, Ill.

[21] Appl. No.: 929,789

[22] Filed: Aug. 13, 1992

[51] Int. Cl.$^5$ .................. A01H 1/00; C12Q 1/68
[52] U.S. Cl. ............................... 47/58; 435/6
[58] Field of Search .................. 47/58.03, 58; 435/172.1, 172.3, 6; 800/205, 235, 255; 935/92, 93, 94, 96, 98

[56] References Cited

PUBLICATIONS

Welsh. 1981. In Fundamentals of Plant Genetics and Breeding. pp. 187-190.
Young et al. 1989 a. Theor Appl. Genet. 77:95-101.
Young et al. 1989b. Theor Appl. Genet. 77:353-359.
Young et al. 1988. Genetics. 120:579-585.
Allard. 1960. In Principles of Plant Breeding. pp. 150-158.
Rayburn and Gill, 1985, J. Hered. 76: 78-81.
Lander and Botstein, 1989, Genetics 121: 185-199.
Zhao et al., 1989, Theor. Appl. Genet. 78: 201-209.
Zischler et al., 1989, Hum. Genet. 82: 227-233.
Hillel et al., 1990, Genetics 124: 783-789.
Itoh et al., 1991, Theor. Appl. Genet. 81: 356-362.

*Primary Examiner*—David T. Fox
*Assistant Examiner*—Erich E. Veitenheimer
*Attorney, Agent, or Firm*—Allegretti & Witcoff, Ltd.

[57] ABSTRACT

This invention provides methods for more efficiently breeding novel species, subspecies or varieties of plants possessing desirable traits derived from other species, subspecies or varieties. In particular, the invention provides reagents and methods for quantitatively determining the genetic contribution from each parent in the progeny of a genetic cross between parental plants of different species, subspecies or varieties. The invention also provides methods for isolating hybrid and backcross progeny plants with a desired trait or combination of traits having inherited the minimum amount of DNA from the trait donor plant. Nucleic acid probes specific for species, subspecies and varieties of plants are also provided.

11 Claims, 2 Drawing Sheets

METHODS AND REAGENTS FOR BACKCROSS BREEDING OF PLANTS

BACKGROUND OF THE INVENTION

1. Field of the Invention

This invention relates to the field of plant breeding. In particular, it relates to methods and reagents for quantitatively determining the genetic contribution of each parent in the progeny of a genetic cross between parental plants of different species, subspecies, or varieties. The invention also provides methods for selecting progeny plants having a desired trait or combination of traits that have inherited a minimum amount of DNA from the trait donor species, subspecies or variety. Reagents comprising nucleic acid probes specific for plant species, subspecies and varieties are also provided by the invention.

2. Description of the Prior Art

Genetic uniformity leads to susceptibility of crop plants, horticultural plants and other useful and economically important plants to many pests and pathogens resulting in widespread epidemics. This is of great concern to the plant breeder. To introduce genetic diversity into these plants, it is often desirable to introduce traits into existing varieties through outcrosses to the exotic or wild species of the same genus. The major drawback of crosses between plants of different species is that large numbers of backcrosses to the existing varieties are necessary to eliminate deleterious and/or undesirable traits present in the progeny that are derived from the exotic or wild species.

Traditional methods of plant breeding following outcrossing involves selection of progeny plants based on phenotypic traits. Although traditional methods are useful in selecting individual characters (e.g., disease resistance), selection of those hydbrid progeny most genetically similar to either of the parental species is inefficient using these methods.

Because those hybrid progeny which have inherited the least amount of DNA from one parent will most genetically resemble the other parent, methods capable of differentiating the relative contribution of each parent to the genomic DNA of the hybrid would be useful in selecting the appropriate hybrids for further propagation by backcross to the desired parental species.

Nucleic acid probes specific for particular species, subspecies or varieties of plants are capable of differentiating between the relative genetic contribution of each parent to the genomic DNA of a progeny plant in a genetic cross between plants of different species, subspecies or varieties. The prior art describes a variety of nucleic acid probes that bind to plant DNA.

Rayburn and Gill, 1985, J. Hered. 76: 78–81 describe the use of biotin-labeled probes to map specific DNA sequences on wheat chromosomes.

Lander and Botstein, 1989, Genetics 121: 185–199 describe the mapping of Mendelian factors using restriction fragment length polymorphisms.

Zhao et al., 1989, Theor. Appl. Genet. 78: 201–209 describe genome-specific repetitive sequences as useful markers for studying plant genome evolution and species divergence.

Zischler et al., 1989, Hum. Genet. 82: 227–233 describe digoxigenated oligonucleotide probes specific for simple repeats and applications of such probes to fingerprinting and in situ hybridization studies.

Hillel et al., 1990, Genetics 124: 783–789 describe the application of DNA fingerprint techniques to introgression plant breeding programs.

Itoh et al., 1991, Theor. Appl. Genet. 81: 356–362 describe studies involving species-specific DNA probes.

SUMMARY OF THE INVENTION

Figure 1:
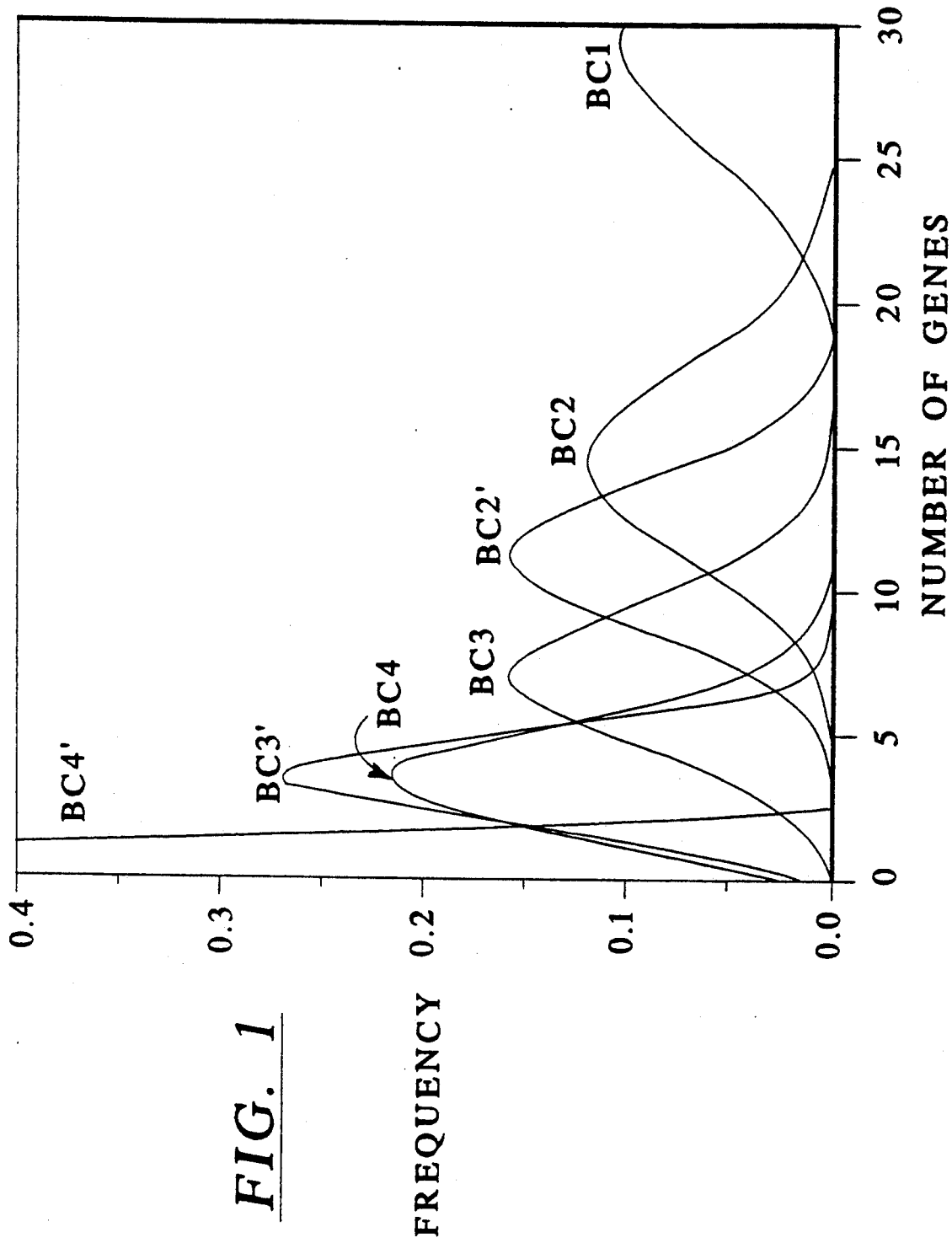
FIG. 1 illustrates a statistical model of marker-assisted introgression.

This invention provides a rapid means of selecting progeny plants in a breeding program that have inherited DNA encoding at least one desired trait derived from a plant of a donor parent of a particular species, subspecies or variety and a minimum amount of DNA from the donor parent, represented in the genomic DNA of the progeny of a genetic cross between the donor parent and a recipient parent. For the purposes of this invention, the term "donor parent" is intended to mean a plant of any species, subspecies or variety possessing a desired trait or combination of traits that is genetically heritable. The term "recipient parent", as used in this invention, is intended to mean a plant of any species, subspecies or variety into which it is desired to introduce a genetic trait or combination of traits from the donor parent.

The methods of the invention comprise transferring DNA from a donor parent plant of one species, subspecies or variety to a recipient plant of a second species, subspecies or variety to produce a viable hybrid plant. For the purposes of this invention, the term "hybrid" is intended to encompass plants produced by a genetic cross between donor parent plants and recipient parent plants (comprising the $F_1$ progeny). The methods of the invention also comprise backcross breeding of such hybrid plants to the recipient parent plants resulting in the generation of backcross progeny plants. For the purposes of this invention, the term "backcross progeny" is intended to include all progeny of backcrosses between $F_1$ hybrid plants and plants of the recipient parent (comprising $BC_1$ progeny), as well as all progeny of backcross between the recipient parent plants and successive generations of backcross progeny (comprising $BC_n$ where $n=2,3,4\ldots$); successive generations of backcross progeny plants are also encompassed by the term "rebackcross progeny", to distinguish such plants from $BC_1$ progeny plants. $F_1$ progeny are backcrossed to the recipient parent plants to produce backcross progeny $BC_1$. Progeny from this cross that have inherited the DNA encoding the desired trait or combination of traits, and may or may not express the desired trait or combination of traits, are selected for further backcross breeding with the recipient parent on the basis of the amount of donor parent DNA contained in the genomic DNA of such progeny. To this end, the genomic DNA of such progeny is quantitatively analyzed using a nucleic acid probe specific for DNA from the donor parent. Plants having the least amount of such donor-derived DNA are then selected for backcross breeding. Progeny plants from such a backcross ($BC_2$; also termed rebackcross progeny) that have inherited the DNA encoding the desired trait or combination of traits, and may or may not express the desired trait or combination of traits, having the least amount of donor parent-derived DNA are then selected for further rounds of backcross breeding (generating backcross progeny plants BC$_3$, BC$_4$, etc.) The invention also encompasses any of the hybrid plants and backcross and rebackcross progeny plants produced and selected using this method. Probes to the recipient parent may also be used in conjunction with or separate from the donor probes in the same manner.

The amount of DNA derived from the donor parent can be selectively minimized, and the amount of recipient parent DNA maximized, in successive generations of backcross progeny. This is advantageous because many unwanted traits as well as the desired trait or combination of traits are inherited from the donor parent by the F$_1$ progeny. Accordingly, the invention provides methods for determining the extent of the genetic contribution of the donor parent in individual backcross progeny, as well as determining the extent of the genetic contribution of the recipient parent. This enables the selection of such progeny for further breeding having the desired trait or combination of traits and comprising a sufficient amount of DNA inherited from the donor parent to carry the desired trait or combination of traits.

It is an advantage of this invention that the number of backcrosses required to transfer a trait or combination of traits into a plant of an existing species, subspecies or variety is significantly reduced. This is because both the DNA contribution of the donor parent and the phenotype may undergo selection in each successive generation using the methods of the invention. For traits that are inherited in a genetically dominant fashion, progeny are selected in each generation that express the desired trait inherited from the donor parent along with the least amount of DNA from the donor parent plant and the greatest amount of DNA from the recipient parent, and thereby most closely resemble the recipient parent plant. Current breeding regimes for introducing an expressed trait into a plant of an existing species, subspecies or variety select on the basis of phenotype alone, thereby requiring a much larger number of backcrosses to the recipient parent to minimize the genetic contribution of the donor parent in the resulting hybrid progeny. For traits that are inherited in a recessive fashion, the present invention enables the selection of progeny in each generation that have inherited the DNA encoding the desired trait from the donor parent (in the absence of phenotypic expression of such trait), along with the least amount of DNA from the donor parent plant and thereby most closely resemble the recipient parent plant. Using current breeding regimes it is both impractical and uneconomical to introduce a recessive trait or combination of traits into an existing plant species, subspecies or variety, due to the inability to directly select for the recessive phenotype.

The invention provides methods and reagents for quantitatively determining the genetic contribution of both the donor and the recipient parents in hybrid plants and in successive generations of backcross progeny plants produced by repetitive backcrossing to plants of the recipient parent species, subspecies or variety. The DNA of the progeny plants possessing the desired trait or combination of traits in each successive generation is quantitatively analyzed using a donor parent specific probe that binds exclusively to the DNA inherited from the donor parent. The hybrid plants and backcross progeny plants having the desired trait or combination of traits and the least amount of DNA from the donor parent that binds to the donor-specific probe are selected in each generation for further propagation by backcrossing to plants of the recipient parent species, subspecies or variety. The invention encompasses hybrid plants and hybrid plant species, subspecies or varieties selected by this method. This method can be used repetitively, and backcross progeny plants produced by such repetitive application of these methods are also encompassed in the invention. F$_1$ hybrid plants and plants of successive generations of backcross progeny (BC$_2$, BC$_3$, etc.) can be similarly quantitatively analyzed using a recipient parent specific probe that specifically binds to the DNA inherited from the recipient parent.

The invention also includes seed from hybrid plants and backcross progeny plants of the invention.

The invention also includes nucleic acid probes specific for plants of species, subspecies or varieties useful in the practice of this invention for quantitatively determining the genetic contribution of donor or recipient parent plants to progeny plants.

Specific preferred embodiments of the present invention will become evident from the following more detailed description of certain preferred embodiments and the claims.

DETAILED DESCRIPTION OF THE PREFERRED EMBODIMENTS

Specific sequences reside in the genomes of each individual of a particular plant species, subspecies or variety. The specificity of such sequences derives from the fact that they are absent in the genomes of the individuals of all other plant species, subspecies or varieties. The utility of such sequences arises from the fact that they can be used to detect DNA derived from one species, subspecies or variety in the genomic DNA of a hybrid or backcross progeny plant produced by a genetic cross between a plant of that specific species, subspecies or variety and a plant of a different species, subspecies or variety. A species-specific probe is capable of detecting sequences present in a particular species that are absent from all other species.

Examples of species-specific genetic sequences are repetitive DNA sequences. Such sequences include but are not limited to short interspersed repeats (SINEs) and long interspersed repeats (LINEs), as well as telomeric sequences and sequences comprising ribosomal RNA genes and others. For example, SINE sequences are repeated with high frequency throughout the entire genome of each individual of a particular species. Because of the high copy number of these sequences in the genome, they are almost always co-inherited with genes of interest. Thus, they are useful in determining the amount of donor parent-derived DNA present in the genomic DNA of a hybrid or backcross progeny plant that has inherited at least one donor parent-derived desireable trait, either phenotypically expressed (i.e., a dominant trait) or not (i.e., a recessive trait).

Highly repetitive DNA represents a substantial amount of the total plant genomic DNA, comprising 20–70% of the genomic DNA in higher plants. Several repeated DNA sequences have been isolated from any different plant species (see, e.g. Plastuch et al., 1990, Mol Gen. Genet. 222: 97; Shepard et al., 1990, Plant Sci. 67: 57; McIntyre et al., 1990, Genome 33: 635; Zhang et al., 1990, Genome 33: 283, Iwabuchi et al., 1991, Theor.

Appl. Genet. 81: 349: Ganal et al., 1988, Mol. Gen. Genet. 213: 262).

In the practice of the present invention, it is useful to develop donor- and recipient-specific nucleic acid probes from each species, subspecies and variety to be used in a breeding program. In order to isolate the largest number of probes from each species, subspecies and variety, all methods of probe isolation are used. The effectiveness of the methods used to isolate donor- and recipient-specific probes is determined using a variety of assays well known to those with skill in the art, including dot blot analysis and Southern blot analysis. These assays are capable of demonstrating that the donor and recipient parent-specific probes so isolated are present in the genomic DNA of each individual of a particular plant species, subspecies or variety at high copy number ($\approx$ >100 copies/haploid genome). Previously, some such species-specific probes have been isolated from many plant species (Lapitan et al., 1986, J. Hered. 77: 415).

Probes provided by the invention include but are not limited to nucleic acid sequences isolated as described hereinbelow, and DNA binding proteins and peptides, as well as probes made synthetically using nucleic acid or amino acid sequence information derived therefrom. The invention specifically includes but is not limited to oligonucleotide, nick-translated, random primed, or in vitro amplified probes, and probes synthesized chemically using nucleotide sequence information derived from the cloned embodiments of the invention.

Probes may be labeled with a detectable moiety, including but not limited to fluorescent moieties, radioactive atoms and chemiluminescent molecules in accordance with known procedures, and can be used in conventional hybridization assays, as described in greater detail in the Examples below.

The exact chromosomal location of the probes that are isolated is determined using a technique known as in situ hybridization. Optimally, the probes used with the methods of this invention are located on every chromosome of a plant of a particular species, subspecies or variety.

Probes useful with the methods of this invention are specific for plants of particular species, subspecies or even particular varieties. Exemplary of such probes are probes that can distinguish between different species (e.g., *Glycine max* and *Glycine soja*) and probes that can distinguish between different cultivars (e.g., *G. max* cultivars Wayne and Williams).

Existing crop plants useful as the source of specific nucleic acid probes of the invention include but are not limited to corn (*Zea mays* L.), rye (*Secale cereale*), wheat (*Triticum aestivum* and *Triticum turdigum*), cotton (*Gossypium hirsutum* and *Gossypium barbadense*), soybean (*Glycine max*), barley (*Hordeum vulgare*), and rice (*Oryza sativa* and *Oryza glaberima*) (see, Simmonds, ed., 1976, *Evolution of Crop Plants*Longman: New York). Wild or exotic plant species useful as the source of specific nucleic acid probes of the invention include but are not limited to teosinte (*Zea luxurians, Zea diploperennis, Zea mays* ssp. *mexicana, Zea mays* ssp. *parviglumis*), *Secale africanum, Glycine soja, Hordeum bulbosum, Oryza nivara, Oryza rufipogen,* and *Oryza perennis.* The methods of the invention are also intended to be useful for the selection of viable hybrids and backcross progeny plants comprising horticultural plants (see, Everett, 1981, *The New York Botanical Garden Illustrated Encyclopaedia of Horticulture*, Garland Publishers: New York] and other economically-important plants, plant species, subspecies and varieties. Most importantly, progeny plants resulting from outcrosses as described herein must contain viable gametes (egg and/or sperm cells) and produce viable seed.

The nucleotide sequence of each individual specific probe isolated as described herein is determined using methods well known to those with skill in the art.

EXAMPLE 1

Species-specific Probe Isolation

To obtain dispersed repetitive DNA sequences useful as species-specific probes, total genomic DNA is isolated and digested with a restriction endonuclease. Gel electrophoresis following DNA digestion results in the production of a continuous smear of DNA fragments of different sizes. Upon staining with ethidium bromide, discrete bands corresponding to ribosomal genes and other repeated DNA sequences can be seen in the gel. The positions of such bands of repetitive DNA and ribosomal DNA within the continuous smear seen on the gel may vary between species, subspecies or variety, indicating that some of the bands may be specific to a given plant species, subspecies or variety. This is easily appreciated by comparing the DNA of *Glycine max* (soybeans) and *Glycine soja* (a wild relative). Polymorphisms (variations) in the size and position of the bands of such repetitive DNAs on the gel are evident. These variations correspond to ribosomal genes or repeated DNA sequences found in one species and absent in the other.

DNA from such species-specific polymorphisms are isolated from agarose gels, purified and cloned in the appropriate restriction sites of bacterial plasmid vectors using methods well known to those in the art (see Sambrook et al., 1989, *Molecular Cloning-A Laboratory Manual,* 2d ed., Cold Spring Harbor Laboratory Press: New York). To rapidly determine species, subspecies or varietal specificity, the cloned nucleic acid is used to probe a dot blot containing DNA isolated from plants of different species, subspecies or varieties, for example, *G. max* and *G. soja*. In such a dot blot analysis, total genomic DNA from *G. max* and *G. soja* is separately placed on a nucleic acid binding membrane at varying concentrations and annealed to each detectably-labeled probe. The intensity of labeling, reflecting the extent of annealing of each probe, is then measured and compared with DNA from each species, subspecies or variety at several standard concentrations. A positive signal means that the DNA sequence from the probe has annealed to the genomic DNA of plants of a particular species, subspecies or variety. Conversely, the absence of a signal using such a probe means that the sequence is not present in that genomic DNA sample. To be specific, probes isolated from one species, subspecies or variety should produce a positive signal exclusively to DNA from that species, subspecies or variety, and probes isolated from that species, subspecies or variety should not produce a positive signal to DNA from any other species, subspecies or variety.

To further determine the specificity of such probes, dot-blot positive probes are used in Southern blot assays (see, Sambrook et al., ibid.). Using this technique, genomic DNA from different species (e.g., *G. max* and *G. soja*) is each separately digested with a restriction endonuclease, resolved on an agarose gel, bound to a membrane and annealed to each labeled probe specific for each species of interest. The specificity of binding between the probe and the genomic DNA noted in the dot-blot assay should be maintained using the Southern blot assay for probes that are truly species-specific. Similarly, Southern blot experiments can be performed to verify subspecies or varietal specificity of such probes.

Regardless of the probe isolation method used (including those described herein), the pattern of the distribution of the probe sequence in genomic DNA can be rapidly determined by isolating high molecular weight DNA (e.g., from *G. max* and *G. soja*) and digesting it with a restriction endonuclease that recognizes an infrequently-occurring DNA sequence (such as *Meganuclease* I). The large DNA fragments thereby produced from both species are resolved on an agarose gel, blotted onto a membrane and separately annealed to labeled probes specific for each species of interest. Many of the DNA fragments from each species will be labeled if the probe sequence is present randomly throughout the genomic DNA of that particular species.

These methods have been utilized to isolate a DNA probe from *Glycine soja*, a compatible wild relative species of *G. max*. This probe does not anneal to genomic DNA from *G. canescens*, an incompatible wild relative of *G. max* and *G. soja*. However, Southern blot experiments have demonstrated that this DNA probe anneals to both *G. max* and *G. soja* and as such is not entirely species-specific. *G. max* and *G. soja* are known to exhibit polymorphisms that suggest the likelihood of successful isolation of species-specific probes from these plant species (William et al., 1991, Nucleic Acids Res. 18: 6531).

ALTERNATIVE EXAMPLE 1

Species-specific Probe Isolation

Species-specific DNA probes can be isolated from genomic libraries prepared from DNA for each species, subspecies or variety of interest using methods well known in the art (Sambrook et al, ibid.). A genomic library consists of a representative sample of the total genomic DNA from a given species, subspecies or variety that has been randomly cloned into a bacterial vector. Subsequently, the genomic DNA in each library is introduced into a suitable bacterial host to generate stable colonies that facilitate manipulations of this DNA. Bacterial colonies comprising bacteria harboring plasmid clones containing plant genomic DNA are transferred onto membrane filters and analyzed by colony hybridization (Sambrook et al., ibid.). Total genomic DNA from each species, subspecies or variety to be used in breeding experiments is labeled and used as a probe for annealing to such filters, wherein each probe is separately annealed to filters prepared from libraries from each species, subspecies or variety of interest. Colonies are selected that specifically anneal to probes from one species and not to others.

To further determine the species-specificity of probes isolated in this fashion, plasmid DNA is isolated from positively-hybridizing bacterial colonies and used as a probe for annealing to dot blots and Southern blots of genomic DNA from plants of different species, subspecies or varieties as described in Example 1.

ALTERNATIVE EXAMPLE 1

Species-specific Probe Isolation

Species-specific DNA probes are isolated on the basis of differential DNA reassociation of regions of DNA present in one species and not the other. There are several techniques known to those in the art that enhance DNA reassociation. These include the use of reagents such as dextran sulfate, polyethylene glycol, phenol and others. The method described herein is known as the phenol emulsion reassociation technique (PERT) and has been coupled to molecular cloning of the desired DNA into a bacterial vector (see Kohne et al., 1977, Biochem. 16: 5329).

Under conditions of the PERT reaction, DNA reassociates several thousand times more rapidly than in aqueous solution. Genomic DNA from one species (e.g., *G. max*) is isolated and sheared to 1000 basepairs in length by sonication. Genomic DNA from a second species (e.g., *G. soja*) is isolated and digested with a restriction endonuclease (e.g., MboI). 25 $\mu$g of sheared DNA from a first species (termed the driver DNA) is then mixed with 0.25 $\mu$g of MboI-digested DNA from a second species (termed the tracer DNA), heated for 5 minutes at 100° C. and immediately submerged in ice. To the DNA solution a mixture of 8% phenol, 1.2 mM NaClO$_4$ and 120 mM sodium phosphate (pH 6.8) is added to a final volume of 1 mL. This solution is intermittently agitated for 5–7 days to form a milky emulsion. Thereafter, the phenol is removed by extraction with chloroform and the salts are removed by dialysis.

The resulting solution contains three types of reassociated DNA molecules. The majority of the DNA molecules consist of reannealed driver DNA having sheared ends. A second class consists of heterologous DNA molecules having one sheared strand from the driver DNA and one MboI-digested strand from the tracer DNA. The rarest type of DNA molecule present in the mixture consists of DNA resulting from the reassociation of two MboI-digested tracer DNA molecules. Such molecules are the only molecules of the three types capable of being cloned into the complementary ends of a BamHI-digested plasmid cloning vector. Such a mixture of reannealed DNA is ligated without separation into such a plasmid cloning vector and used to transform bacteria. Bacterial colonies are then screened by colony hybridization with labeled total genomic DNA to detect tracer DNA-specific inserts, and DNA isolated from these bacterial colonies is used in dot bot and Southern blot assays as described in Example 1 above. Species-specific probes are expected to anneal intensely to labeled tracer DNA and not at all to labeled driver DNA. In order to isolate driver-specific DNA probes, the experiment described herein is repeated so that the driver DNA as described herein is now the tracer DNA (0.25 $\mu$g) and the tracer DNA as described herein is the driver DNA (25 $\mu$g).

EXAMPLE 2

Chromosome Localization of Species-Specific Probes

The chromosomal location of species-specific probes isolated as described in Example 1 are determined using in situ hybridization techniques. The results of such experiments detect the presence and chromosomal location of such probes within the genomic DNA of the parental plants and hybrid and backcross progeny plants.

Some species-specific probes are scattered randomly throughout the genome at a relatively high density. In situ hybridization techniques well known to those in the art are used to determine the precise chromosomal location of such probes. Chromosomes from root-tip cells arrested at metaphase with colchicine or by cold treatment are fixed onto a microscope slide and annealed to labeled nucleic acid probes (see Lapitan et al., 1986, J. Hered. 77: 415). The chromosomal location of each species-specific probe is then determined microscopically.

More specifically, root tips from both G. max and G. soja species are harvested and incubated with colchine or by cold treatment to arrest the cells at metaphase, where the chromosomes are condensed. These cells are then fixed in an ethanol/acetic acid solution or other fixative well known in the art, placed onto a glass slide and chemically stained to allow the chromosomes to be visualized. A cover slip is added to the slide and the cells disrupted by finger pressure, thereby releasing the chromosomes. The chromosomes are then treated with proteinase K to remove any proteins that could interfere with the annealing reaction to the labeled probe. Each labeled DNA probe previously isolated from each species is annealed to the liberated root chromosomes under stringency conditions similar to those used in Southern blot experiments described in Example 1. The chromosomal location of each probe is identified by detecting a positive signal localized over one or more chromosomes resulting from annealing of the probe. These methods are also capable of determining the identity and chromosomal location of varietal-specific probes (e.g., probes specific for G. max varieties Wayne and Williams).

EXAMPLE 3

Breeding Strategies

Outcrosses can only be performed where the resulting progeny plants contain viable gametes (egg and/or sperm cells). Crosses are performed using techniques well known to plant breeders (see, Fehr, 1987, *Principles of Cultivar Development*, vols. 1&2, MacMillan Publishing: New York), where one species is the donor (donor parent) that expresses a desired trait or combination of traits, and another species is the recipient (recipient parent). Hybrid plants ($F_1$) that have inherited DNA encoding a desired trait or combination of traits (whether or not such a trait is phenotypically expressed in such hybrids) are then backcrossed to plants of the recipient parental species, and those backcross progeny plants that inherit the DNA encoding the desired trait or combination of traits are selected (whether or not such a trait is phenotypically expressed in such backcross progeny plants). The genomic DNA of such backcross progeny plants ($BC_1$) is then analyzed by dot blots and Southern blots using donor parent-specific probes to determine which individual $BC_1$ progeny contain the least amount of donor-specific (donor parent derived) DNA. The contribution of the recipient parent is also analyzed using recipient parent-specific probes. These individuals that have inherited the greatest amount of recipient parent DNA are then selected for further propagation by backcross breeding, if desired. Successive generations may be backcrossed until the DNA content of backcross progeny that have inherited DNA encoding the desired trait or combination of traits (whether or not such a trait is phenotypically expressed) most closely resembles that of the recipient parent (i.e., such progeny have inherited the minimal amount of donor parent-derived DNA). An advantage of the analysis of the genetic contribution of the recipient parent as well as that of the donor parent is that the results of these independent analyses confirm on another.

Crosses are also performed where the donor is a plant of one variety or subspecies and the recipient is a plant of another variety or subspecies within the same species. The relative amount of genomic DNA inherited from each parental variety or subspecies in the resulting hybrid plants and backcross progeny plants is determined using probes specific for each variety or subspecies using the methods described above. Iterative backcrossing of successive generations of such plants to the recipient parental variety or subspecies is then performed as described herein. Plants with the desired phenotype are selected that have a DNA content most similar to the recipient parent variety or subspecies. Genetic transfer of desired traits can be efficiently achieved using these methods.

1. Breeding Strategy Example #1—The Intervarietal Cross

A cross is performed where G. max (variety Williams) is the donor parent and G. max (variety Wayne) is the recipient parent. The relative DNA content of the genomic DNA of the hybrid plants produced by this cross is determined using probes specific for each variety. A backcross of $F_1$ plants (hybrids of Williams×Wayne) with the recipient parent (Wayne) is performed and the relative contribution of each parental variety to the genomic DNA from individual backcross progeny is determined using these probes. Backcross progeny plants that express the desired phenotype are selected having a DNA content most similar to the Wayne variety. Successive generations are backcrossed until the DNA content of individual backcross progeny plants is sufficiently similar to the Wayne variety that the characteristics of the backcross progeny are similar to G. max (variety Wayne), and these backcross progeny plants express the desired phenotype inherited from G. max (variety Williams). Because both the DNA content and the phenotype are examined at each generation (in contrast with traditional breeding strategies, which examine only phenotypic characteristics), the number of backcrosses needed to transfer a trait to a progeny plant that is otherwise substantially genetically identical to the recipient parent plant is significantly reduced.

A great advantage of the methods of this invention is the reduction in the time and labor needed to achieve a successful breeding program for introducing a desired trait or combination of traits into a plant species, subspecies or variety. Using these methods, valuable traits are recognized and hybrid and backcross progeny plants appropriate for continued breeding are efficiently selected. Importantly, the time required for backcrossing the desired trait or combination of traits into a plant species, subspecies or variety is significantly reduced. Using the quantitative approach outlined herein, the number of individual progeny plants needed for backcrosses can be pre-determined, prior to planting. Thus, the number of plants grown for these purposes can also be reduced. The actual reduction in breeding time is demonstrated for soybeans in FIGS. 1 and 2.

FIG. 1 represents a statistical model for marker-assisted introgression of soybeans. The model is based on the genetic map size of the soybean genome (approximately 3000 cM) having 60 independently-assorting chromosomal regions. $F_1$ hybrids are produced from the cross of parent A (the donor parent) with parent B (the recipient parent). The $F_1$ hybrid contains 60 heterozygous chromosomal regions. The first generation backcross hybrids ($BC_1$) have an average heterozygous (i.e., donor parent-derived) chromosome distribution of 30. The distribution of heterozygous chromosomes represented by the $BC_2'$ curve, on the other hand, was obtained from the expected results of crosses using representative individuals from the $BC_1$ generation with selection for those 10 out of 100 $BC_1$ individuals having a DNA content most similar to the recipient parent. These methods were repeated for the third and fourth backcross generations, comprising $BC_3'$ and $BC_4'$, respectively. By the fourth generation, it is apparent that most independently-assorting chromosomal regions from the donor parent have been eliminated from the plants produced by backcross breeding of those individual plants at each generation having a DNA content most similar to the recipient parent (see the $BC_4'$ data in FIG. 1). The number of backcrosses needed to achieve this result has been substantially reduced thereby compared to a minimum of six backcrosses used in traditional breeding methods. Curves in FIG. 1 represented by $BC_n$ are derived from calculations of backcross breeding experiments in the absence of selection of those 10 out of 100 plants in each generation having a DNA content most similar to the recipient parent.

Figure 2:
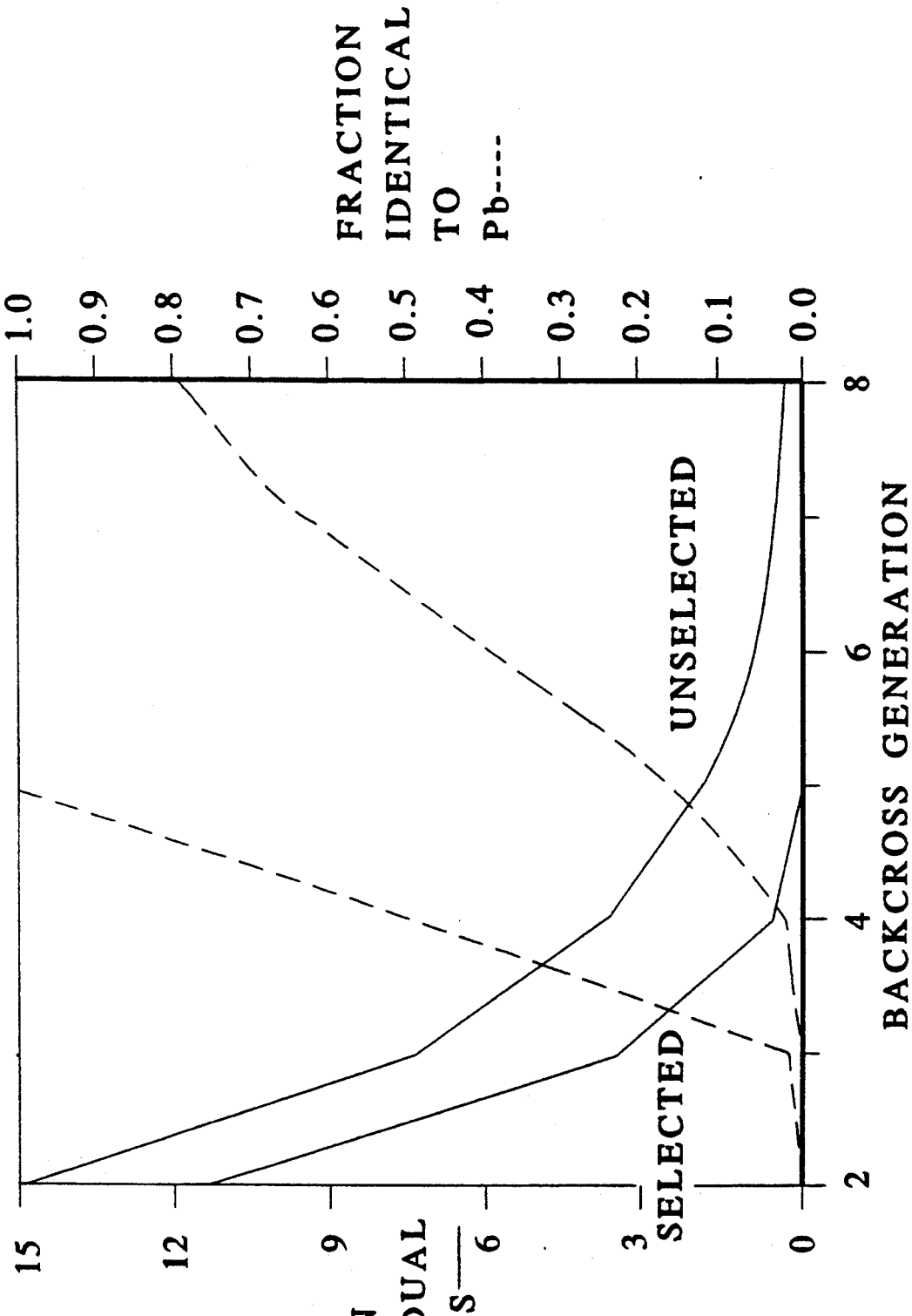
FIG. 2 illustrates the mean of the chromosomal distribution in successive generations of backcross progeny plants.

FIG. 2 illustrates the means of the heterozygous chromosome distribution at each generation (solid lines) and the fraction of plants in each generation that differs from the recipient parent only by the presence of the introgressed region carrying the gene for the desired trait derived from donor parent DNA (dotted line; Pb indicates the recipient parent plant). Using selection for the individual progeny that have inherited the least amount of DNA from the donor parent, the introgression process is essentially complete after the fourth generation. Individuals in subsequent generations do not have any extraneous DNA inherited from the donor parent that is unlinked to the region responsible for expression of the desired trait.

The methods of this invention make crosses between existing species, subspecies or varieties and wild or exotic species economically feasible. Even though many valuable traits are found in wild species, the genetic diversity that produces such traits makes introduction of genes for useful traits difficult and time-consuming using traditional breeding methods. This is because deleterious, harmful traits, that have been bred out of crop plants over many generation of domestication, are reintroduced along with the desirable traits. This necessitates extensive backcross breeding to obtain plants expressing the desired trait or combination of traits that are substantially identical to the existing inbred line or variety. Using the methods of this invention reduces the time and extent of backcross breeding necessary to restore the genetic identity of such progeny plants that express the desired trait or combination of traits.

In addition, both genetically dominant and recessive traits can be introduced using the methods of this invention. Moreover, the use of specific probes to quantitate the amount of DNA inherited from each parent eliminates the need to employ more labor-intensive procedures known in the art wherein traits are scored individually, such as restriction fragment length polymorphism (RFLP) analysis, random amplified polymorphic DNA (RAPD) analysis or DNA fingerprinting.

Non-radioactive probe labeling and detection methods can be using for genome analysis, thereby avoiding complex and expensive waste disposal problems.

Finally, the methods of this invention are not encumbered by the regulatory restrictions placed on methods employing recombinant DNA technology. The methods of this invention utilize established plant breeding techniques. New seed lines generated using these methods are not transgenic.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for obtaining plants with a desired trait or combination of traits comprising:
   a. performing a genetic cross between a donor plant of a first species, subspecies or variety, having a desired trait or combination of traits and a recipient plant of a second species, subspecies or variety, respectively, to form a viable hybrid plant;
   b. backcrossing the hybrid plant of subpart (a) with a plant of the recipient species, subspecies or variety, respectively, to form a viable backcross progeny plant;
   c. quantitatively annealing DNA from individual backcross progeny plants produced in subpart (b) with a detectably-labeled probe or multiplicity of detectably-labeled probes that specifically binds to a plurality of probe binding sites in the DNA from the donor plant species, subspecies or variety and does not bind to the DNA of the recipient plant species, subspecies or variety, respectively;
   d. determining the amount of DNA in each backcross progeny plant inherited from the donor species, subspecies or variety, respectively, that binds to the detectably-labeled probe or multiplicity of detectably-labeled probes, scored as a pool and independent of a physical or genetic map of probe binding sites; and
   e. selecting for further propagation the backcross progeny plants having the desired trait or combination of traits that have inherited the least amount of DNA from the donor species, subspecies or variety.

2. The method of claim 1 wherein the backcross progeny plants inherit DNA encoding the desired trait or combination of traits whereby the trait or combination of traits are recessive and do not express a detectable phenotype.

3. The method of claim 1, optionally comprising the following steps:
   f. quantitatively annealing DNA from individual backcross progeny plants produced in subpart (b) with a detectably-labeled probe or multiplicity of detectably-labeled probes that specifically binds to a plurality of probe binding sites in the DNA from the recipient plant species, subspecies or variety and does not bind to the DNA of the donor plant species, subspecies or variety, respectively;
   g. determining the amount of DNA in each backcross progeny plant inherited from the recipient plant species, subspecies or variety, respectively, that binds to the detectably-labeled probe or multiplicity of detectably-labeled probes, scored as a pool and independent of a physical or genetic map of probe binding sites; and h. selecting for further propagation the backcross progeny plants having the desired trait or combination of traits that have inherited the greatest amount of DNA from the recipient plant species, subspecies or variety, respectively;

4. The method of claim 3 wherein the backcross progeny plants inherit DNA encoding the desired trait or combination of traits whereby the trait or combination of traits are recessive and do not express a detectable phenotype.

5. A method for obtaining plants with a desired trait or combination of traits comprising:
   a. crossing the backcross progeny plant of subpart (e) of claim 1 with a plant of the recipient species, subspecies or variety, respectively of claim 1 to produce a rebackcross progeny plant having the desired trait or combination of traits;
   b. quantitatively annealing DNA from individual rebackcross progeny plants produced in subpart (a) with a detectably-labeled probe or multiplicity of detectably-labeled probes that specifically binds to a plurality of probe binding sites in the DNA from the donor plant species, subspecies or variety of claim 1 and does not bind to the DNA of the recipient plant species, subspecies or variety, respectively;
   c. determining the amount of DNA in each rebackcross progeny plant of subpart (a) that is inherited from the donor plant species, subspecies or variety, respectively that binds to the detectably-labeled probe or multiplicity of detectably-labeled probes, scored as a pool and independent of a physical or genetic map of probe binding sites; and
   d. selecting for further propagation the rebackcross progeny plants of subpart (a) having the desired trait or combination of traits that have inherited the least amount of DNA from the donor plant species, subspecies or variety, respectively of claim 1.

6. The method of claim 5 wherein the backcross progeny plants inherit DNA encoding the desired trait or combination of traits whereby the trait or combination of traits are recessive and do not express a detectable phenotype.

7. The method of claim 5 wherein the rebackcross progeny plants inherit DNA encoding the desired trait or combination of traits whereby the trait or combination of traits are recessive and do not express a detectable phenotype.

8. The method of claim 5, optionally comprising the following steps:
   e. quantitatively annealing DNA from individual rebackcross progeny plants produced in subpart (a) with a detectably-labeled probe or multiplicity of detectably-labeled probes that specifically binds to a plurality of probe binding sites in the DNA from the recipient plant species, subspecies or variety and does not bind to the DNA of the donor plant species, subspecies or variety, respectively;
   f. determining the amount of DNA in each rebackcross progeny plant inherited from the recipient plant species, subspecies or variety, respectively, that binds to the detectably-labeled probe or multiplicity of detectably-labeled probes, scored as a pool and independent of a physical or genetic map of probe binding sites; and
   g. selecting for further propagation the rebackcross progeny plants having the desired trait or combination of traits that have inherited the greatest amount of DNA from the recipient plant species, subspecies or variety, respectively.

9. The method of claim 8 wherein the rebackcross progeny plants inherit DNA encoding the desired trait or combination of traits whereby the trait or combination of traits are recessive and do not express a detectable phenotype.

10. A method for selecting plants with a desired trait or combination of traits comprising performing steps (a) through (d) of the method of claim 5 with each successive generation of backcross progeny plants.

11. A method for selecting plants with a desired trait or combination of traits comprising performing steps (a) through (g) of the method of claim 8 with each successive generation of backcross progeny plants.

* * * * *